United States Patent [19]

Dziabo et al.

[11] Patent Number: 5,338,480
[45] Date of Patent: Aug. 16, 1994

[54] COMPOSITIONS AND METHODS TO CLEAN CONTACT LENSES

[75] Inventors: Anthony J. Dziabo, El Toro; Hampar Karageozian, Laguna Hills; Paul S. Ripley, Irvine; Sam W. Lam, Laguna Niguel; J. Abraham Espiritu, Oceanside, all of Calif.

[73] Assignee: Allegan, Inc., Irvine, Calif.

[21] Appl. No.: 664,601

[22] Filed: Mar. 4, 1991

Related U.S. Application Data

[63] Continuation-in-part of Ser. No. 416,074, Oct. 2, 1989, Pat. No. 5,078,908, and a continuation-in-part of Ser. No. 461,405, Jan. 5, 1990, and a continuation-in-part of Ser. No. 461,540, Jan. 5, 1990, Pat. No. 4,997,626.

[51] Int. Cl.$^5$ .......................... A61L 2/18; A61L 2/20
[52] U.S. Cl. .......................... 252/187.21; 252/187.23; 252/187.25; 252/187.26; 252/187.27; 435/264; 424/661; 424/662
[58] Field of Search .......... 252/187.21, 187.23, 252/187.25, 187.26, 187.27; 424/663, 661, 662; 435/264

[56] References Cited

U.S. PATENT DOCUMENTS

| | | | |
|---|---|---|---|
| Re. 23,218 | 4/1950 | Levy | 162/87 |
| Re. 31,779 | 12/1984 | Alliger | 56/284 |
| Re. 32,672 | 5/1988 | Huth et al. | 252/174.12 X |
| 2,436,134 | 2/1948 | Aston | 252/186.22 |
| 3,123,521 | 3/1964 | Wentworth | 424/615 |
| 3,278,447 | 10/1966 | McNicholas | 252/186.21 |
| 3,591,515 | 7/1971 | Lovely | 252/186.22 |
| 3,819,828 | 6/1974 | McCoy | 424/71 |
| 3,910,296 | 10/1975 | Karageozian et al. | 134/2 |
| 3,912,451 | 10/1975 | Gaglia, Jr. | 422/30 |
| 4,011,941 | 3/1977 | Parsons | 432/21 |
| 4,084,747 | 3/1978 | Alliger | 422/20 |
| 4,104,190 | 8/1978 | Hartshorn | 252/187.21 |
| 4,123,376 | 10/1978 | Gray | 252/99 |
| 4,146,496 | 3/1979 | Gray | 252/99 |
| 4,386,160 | 5/1983 | Branner-Jorgensen | 435/221 |
| 4,456,510 | 6/1984 | Murakami | 204/101 |
| 4,459,217 | 7/1984 | Bogie | 252/174.14 |
| 4,499,077 | 2/1985 | Stockel et al. | 424/661 |
| 4,557,925 | 12/1985 | Lindahl et al. | 424/482 |
| 4,568,517 | 2/1986 | Kaspar et al. | 422/30 |
| 4,614,549 | 9/1986 | Ogunbuyi et al. | 134/19 |
| 4,618,444 | 10/1986 | Hudson et al. | 252/92 |
| 4,654,208 | 3/1987 | Stockel et al. | 424/661 |
| 4,689,215 | 8/1987 | Ratcliff | 424/53 |
| 4,690,773 | 9/1987 | Ogunbuyi et al. | 252/174.12 |
| 4,767,559 | 8/1988 | Kruse et al. | 252/186.21 |
| 4,792,442 | 12/1988 | Ratcliff | 395/200 |
| 4,855,135 | 8/1989 | Ratcliff | 424/661 |
| 4,861,514 | 8/1989 | Hutchings | 252/187.21 |
| 4,986,990 | 1/1991 | Davidson et al. | 424/665 |

(List continued on next page.)

FOREIGN PATENT DOCUMENTS 520668 12/1987 Australia .

(List continued on next page.)

OTHER PUBLICATIONS

Communications to the Editor, "Stabilization of Microbial Proteases against Autolysis Using Acylation with Dicarboxylic Acid Anhydrides", Biotechnology and Bioengineering, vol. XXIV, pp. 483–486(1982).

(List continued on next page.)

Primary Examiner—Robert L. Stoll
Assistant Examiner—Valerie Fee
Attorney, Agent, or Firm—Frank J. Uxa

[57] ABSTRACT

Compositions and methods to clean contact lenses are disclosed. In one embodiment, the present composition comprises at least at least one enzyme capable of removing debris from a contact lens and at least one disinfectant destroying component capable of destroying a contact lens disinfectant which is incompatible with the at least one enzyme. The composition is structured so that the at least one enzyme is released in a liquid medium containing the contact lens disinfectant at substantially the same time or after the at least one disinfectant destroying component is released in the liquid medium, thereby allowing the at least one enzyme to remove debris from a contact lens in the liquid medium.

25 Claims, No Drawings

U.S. PATENT DOCUMENTS

| | | | |
|---|---|---|---|
| 4,997,626 | 3/1991 | Dziabo et al. | 422/37 |
| 5,077,258 | 12/1991 | Phillips | 502/321 |
| 5,078,908 | 1/1992 | Ripley et al. | 252/187.21 |
| 5,129,999 | 7/1992 | Holland et al. | 204/131 |
| 5,135,623 | 8/1992 | Dziabo et al. | 204/101 |
| 5,152,912 | 10/1992 | Dziabo | 252/106 |

FOREIGN PATENT DOCUMENTS

| | | |
|---|---|---|
| 0082798 | 6/1983 | European Pat. Off. |
| 0147100 | 7/1985 | European Pat. Off. |
| 0168253 | 1/1986 | European Pat. Off. |
| 0196075 | 1/1986 | European Pat. Off. |
| 0199385 | 10/1986 | European Pat. Off. |
| 0209071 | 1/1987 | European Pat. Off. |
| 0240315 | 10/1987 | European Pat. Off. |
| 0279401 | 2/1988 | European Pat. Off. |
| 0255041A1 | 5/1988 | European Pat. Off. |
| 0278224 | 8/1988 | European Pat. Off. |
| 0384666 | 2/1990 | European Pat. Off. |
| 0426489 | 5/1991 | European Pat. Off. |
| 0458578A1 | 11/1991 | European Pat. Off. |
| 3626082 | 11/1988 | Fed. Rep. of Germany |
| WO8504107 | 9/1985 | PCT Int'l Appl. |
| WO8605695 | 10/1986 | PCT Int'l Appl. |
| WO8911878 | 12/1989 | PCT Int'l Appl. |
| WO9006126 | 6/1990 | PCT Int'l Appl. |
| WO9109630 | 7/1991 | PCT Int'l Appl. |
| WO9109632 | 7/1991 | PCT Int'l Appl. |
| WO9109690 | 7/1991 | PCT Int'l Appl. |
| WO9215334 | 9/1992 | PCT Int'l Appl. |
| 1269677 | 4/1982 | United Kingdom |
| 2139260A | 11/1984 | United Kingdom |
| 2173017A | 10/1986 | United Kingdom |
| 2187748A | 9/1987 | United Kingdom |
| 2187748 | 9/1987 | United Kingdom |
| 2151039 | 7/1988 | United Kingdom |

OTHER PUBLICATIONS

Kennedy et al, "The Oxidation of Organic Substances by Potassium Peroxymonosulfate", J. Organic Chemistry 25:1901–1906 (1960).

Polymers Letters Edition, "A Study of Ozone Attack On Elastomer Surfaces By Attenuated Total reflectance Spectroscopy", vol. 12, pp. 281–286 (1974).

Manivannan et al, "Peroxo Salts As Initiators Of Vinyl Polymerization—III" Eur. Polym. J. vol. 23, No. 4, pp. 311–313 (1987).

Evans et al, "Phase Transfer Controlled Selective Oxidation Of Diarylsulfides to Diarylsulfoxides Using Potassium Hydrogen Persulfate", Synthetic Communications, 16(10), 1207–1216 (1986).

Bloch et al, "Epoxidation of Alkenes with Potassium Hydrogen Persulfate" J. Org. Chem. 1985, 50, 1544–1545.

Ball, Jr. et al., "Acylation of Egg White Proteins with Acetic Anhydride and Succinic Anhydride", Poultry Science 1982 61:1041–1046.

W. Masschelein, "Preparation of Pure Chlorine Dioxide", vol. 6, No. 2, Jun. 1967.

I. Klotz, "Succinylation", Methods in Enzymology, vol. XI, Enzyme Structure, 1967, 576–580.

De Poorter et al, "Oxone As Oxygen Donor In The Catalytic Hydroxylation Of Saturated Hydrocarbons", Tetrahedron Letters, vol. 26, No. 37, pp. 4459–4462 (1985).

Trost et al, "Chemoselective Oxidation of Sulfides to Sulfones with Potassium Hydrogen Persulfate", Tetrahedron Letters, vol. 22, No. 14, pp. 1287–1290(1981).

Siu et al, "Effect of Succinylation on the Protein Quality and Urinary Excretion of Bound and Free Amino Acids", J. Agric. Food Chem. 1982, 30, 1179–1183.

Chemical Abstracts Selects: Issue 2, 1987.

Eudragit L Data Sheet (Info L-2/e).

COMPOSITIONS AND METHODS TO CLEAN CONTACT LENSES

This application is a continuation-in-part of each of the following copending applications: Ser. No. 416,074 now U.S. Pat. No. 5,078,908 filed Oct. 2, 1989; Ser. No. 461,405 filed Jan. 5, 1990 now pending; and Ser. No 461,540 filed Jan. 5, 1990 now U.S. Pat. No. 4,997,626. Each of these applications is incorporated in its entirety by reference herein.

BACKGROUND OF THE INVENTION

This invention relates to cleaning lenses, such as contact lenses. In particular, the invention relates to compositions and methods useful to quickly and effectively enzymatically clean contact lenses.

Contact lenses should be periodically disinfected and cleaned to protect the wearer's eyes from infection and to improve the wearer's comfort. It is often desirable that lens disinfecting be accomplished quickly, e.g., for the convenience of the wearer. However, conventional fast-acting disinfectants that are used with contact lenses have a high potential to cause eye irritation. A disinfectant which can be easily and effectively dissipated after use would be advantageous to reduce the chance of eye irritation.

In addition to being disinfected, the contact lens should be cleaned, e.g., of protein-based debris which accumulates on the lens during use. Such lens cleaning is often done in the presence of one or more enzymes. See, for example, Karageozian U.S. Pat. No. 3,910,296. In many instances, a complete lens maintenance procedure involves first enzymatic cleaning followed by a separate lens disinfecting step. It would be advantageous to provide for disinfecting and cleaning contact lenses in a one-step procedure.

SUMMARY OF THE INVENTION

New compositions and methods for cleaning lenses, in particular contact lenses, have been discovered. These compositions and methods are particularly applicable when used in conjunction with procedures to disinfect the lenses. Thus, using the present invention, a contact lens can be conveniently and effectively disinfected and cleaned in a sequential manner in the same container. Chlorine dioxide has been found to be a very effective contact lens disinfectant. The chlorine dioxide is effective as a contact lens disinfectant without requiring the presence of other germicides. Thus, chlorine dioxide canbe the sole contact lens disinfectant. However, it has been found that the disinfectant chlorine dioxide is incompatible with many enzymes which can be used to remove (clean) debris from a contact lens. In other words, the disinfectant component, sometimes even in concentrations less than useful as an effective disinfectant, acts to inactivate or otherwise destroy the effectiveness of such enzymes in contact lens cleaning service so that simultaneous lens disinfecting/cleaning is not practical. The present invention overcomes the problems caused by this disinfectant/enzyme incompatibility while providing for safe, effective and efficient disinfecting and cleaning of contact lenses.

In one aspect of the invention, a contact lens is contacted with at least one enzyme capable of removing debris, for example, protein-based debris, from a contact lens in an amount effective to remove debris from the contact lens. This removal or cleaning step is preferably conducted after the lens is disinfected. Thus, in one embodiment, the present method comprises contacting a contact lens, in particular a disinfected contact leds, with a liquid medium containing a disinfectant component in the presence of a composition comprising at least one enzyme which is incompatible with the disinfectant component and is capable of removing debris from a contact lens and at least one disinfectant destroying component capable of destroying the disinfectant component after being released in the liquid medium. The composition is structured to release the enzyme in the liquid medium at substantially the same time or after the disinfectant destroying component is released in the liquid medium. The enzyme and disinfectant destroying component are released in the liquid medium and debris, e.g., proteinaceous debris, is removed from the contact lens in the liquid medium. Contact lens cleaning compositions, for example, compositions structured as described above, are also within the scope of the present invention.

Overall, the present method and compositions are very effective and easy to use. This encourages the lens wearer to disinfect and clean his/her contact lenses frequently, resulting in more comfort and less eye irritation.

DETAILED DESCRIPTION OF THE INVENTION

The present system is applicable for cleaning all types of lenses, e.g., contact lenses. Such lenses, for example, conventional hard contact lenses and soft contact lenses, may be made of any material or combination of materials and may have any suitable configuration.

The lens is subjected to the action of at least one enzyme to remove debris, preferably after disinfecting the lens. This enzyme/lens contacting occurs in a liquid medium, preferably an aqueous liquid medium, such as described elsewhere herein. In a particularly useful embodiment, the enzyme/lens contacting occurs in the same container as does the lens disinfecting, more particularly in the same liquid medium as does the lens disinfecting. This "one-step" disinfecting/cleaning system is effective and very convenient for the lens wearer to use.

Among the types of debris that form on contact lens during normal use are protein-based or proteinaceous debris, mucin-based debris, lipid-based debris and carbohydrate-based debris. One or more types of debris may be present on a single contact lens.

The enzyme or enzymes used are capable of removing at least one type of debris from a contact lens. The amount of such enzyme or enzymes used is preferably effective to remove substantially all of at least one type of debris from a debris laden contact lens in a reasonable time, preferably within about 12 hours, for example, in the range of about 1 minute to about 12 hours, and more preferably within about 2 hours, for example, about 1 minute to about 2 hours. The active enzyme-containing liquid medium preferably contains sufficient enzyme to provide between about 0.0001 to about 5 Anson units of activity, more preferably between about 0.001 or about 0.01 to about 0.1 or about 1 Anson unit, per single lens treatment. Higher or lower amounts may be used.

The enzyme employed may be selected from enzymes which are conventionally employed in the enzymatic cleaning of contact lenses. For example, many of the enzymes disclosed in Huth et al. U.S. Re. No. 32,672 and Karageozian et al. U.S. Pat. No. 3,910,296 are useful in the present invention. Each of these patents is incorporated in its entirety by reference herein. Among the useful enzymes are those selected from proteolytic enzymeS, lipases and mixtures thereof. The enzyme may be one or more carbohydrate-active or carbolytic enzymes, lipases and mixtures thereof. The enzyme proteases, amylases, lipases and mixtures thereof.

Preferred proteolytic enzymes are those which are substantially free of sulfhydryt groups or disulfide bonds. Metallo-proteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacteria and Asperigillus molds. Within this grouping, the still more preferred enzymes are the derived alkaline proteases generically called subtilisin enzymes. Reference is made to Deayl, L., Moser, P. W. and Wildi. B. S., "Proteases of the Genus Bacillus. II Alkaline Proteases", Biotechnology and Bioengineering, Vol. XII, pp 213-249 (1970) and Keay, L. and Moser, P. W., "Differentiation of Alkaline Proteases form Bacillus Species" Biochemical and Biophysical Research Comm., Vol 34, No. 5, pp 600–604, (1969).

The subtilisin enzymes are broken down into two subclasses, subtilisin A and subtilisin B. In the subtilisin A grouping are enzymes derived from such species are *B. subtills, B. licheniformis* and *B. pumilis.* Organisms in this sub-class produce little or no neutral protease or amylase. The subtilisin B sub-class is made up of enzymes from such organisms a *B. subtills, B. subtills var. amylosacchariticus, B. amyloliquefaciens* and *B. subtills* NRRL B3411. These organisms produce neutral proteases and amylases on a level about comparable to their alkaline protease production. One or more enzymes from the subtilisin A sub-class are particularly useful.

In addition other preferred enzymes are, for example, pancreatin, trypsin, collaginase, keratinase, carboxylase, aminopeptidase, elastase, and aspergillo-peptidase A and B, pronase E (from *S. griseus*) and dispase (from *Bacillus polymyxa*).

An effective amount of enzyme is to be used in the practice of this invention. Such amount will be that amount which effects removal in a reasonable time (for example overnight) of substantially all of at least one type of debris from a lens deposited due to normal wear. This standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective lens cleaner will depend on several factors, including the inherent activity of the enzyme.

Enzyme activity is pH dependent so for any given enzyme, there is a particular pH range in which that enzyme will function best. The determination of such range can readily be done by known techniques.

It has been found that many of the effective lens cleaning enzymes, such as described elsewhere herein, are inactivated in the presence of certain contact lens disinfectants. For example, a substantial number of such enzymes are inactive in the presence of disinfecting amounts of chlorine dioxide. Since the use of such enzyme incompatible (or simply incompatible) contact lens disinfectants is often advantageous in the contact lens disinfecting context, a system to allow both such disinfecting and enzymatic cleaning of contact lenses, preferably in one user initiated step, would clearly be advantageous. The present invention provides such a system.

The present composition comprises an effective debris removing amount of at least one enzyme capable of removing debris from a contact lens and at least one disinfectant destroying component capable of destroying a contact lens disinfectant which is incompatible with the enzyme, such as chlorine dioxide. Whether or not any specific contact lens disinfectant is incompatible with any specific lens cleaning enzyme can be determined simply by observing the lens cleaning activity or inactivity of the enzyme in the presence of the disinfectant. Other incompatible contact lens disinfectants may include, for example, potassium peroxymonosulfate, quaternary disinfectants,, such as quaternary ammonium disinfectants, and the like. In any event, the composition is structured, such as in a delayed release configuration, so that the enzyme is released in a liquid medium containing the disinfectant at substantially the same time or after the disinfectant destroying component is released in the liquid medium. Using this composition, the enzyme is allowed to remove debris from the contact lens in the liquid medium, with no substantial interference from the disinfectant.

In a particularly useful embodiment where the incompatible disinfectant is chlorine dioxide, the enzyme can be present in a delayed release form together with a chlorine dioxide destroying component, preferably a chlorine dioxide reducing component or agent, such as N-acetylcysteine and the like, effective to chemically reduce chlorine dioxide in a liquid medium. In this embodiment, the enzyme is released after the lens in disinfected. Thus, the enzyme is released at substantially the same time or after the chlorine dioxide destroying component and acts to clean the disinfected lens, with no substantial interference from chlorine dioxide.

Any suitable disinfectant destroying component may be used in the present invention, provided that it functions as described herein and has no substantial detrimental effect on the lens being treated and on the human wearing the treated lens. In the case of chlorine dioxide disinfectant, a chlorine dioxide reducing agent or component is preferably included in the disinfectant destroying component to chemically reduce the chlorine dioxide, more preferably substantially all the chlorine dioxide remaining in the liquid medium, particularly after the lens is disinfected.

Any suitable chlorine dioxide reducing agent may be used in the present invention, provided that it functions as described herein and has no substantial detrimental effect on the lens being treated and on the human wearing the treated lens. Examples of useful reducing agents include, but are not limited to, SH (group)—containing water soluble lower alcohols, N-acetylcysteine, acetylcysteine, cysteine hydrochloride ethyl ester, glutathione, homocysteine, carbamoylcysteine, cysteine, cysteine hydrochloride, dithiothreitol, sodium bisulfite, thio urea, beta-mercaptoethanol, cysteinyl glycine, 2-mercaptopropionic acid, 2-mercaptopropionylglycine, 2-mercaptoethylamine hydrochloride, dithioerythritol, sodium metabisulfite, sulfites, pyrosulfites, dithionites and the like. A particularly useful example of such a reducing agent is N-acetylcysteine. The amount of the reducing agent used is such to chemically reduce the desired amount of chlorine dioxide. In one embodiment, the amount of reducing agent employed is about 50% to about 150% that amount needed to chemically reduce all the chlorine dioxide present in the liquid medium when the reducing agent is released in the liquid medium. The amount of reducing agent used is preferably at least that amount needed to chemically reduce all the chlorine dioxide present in the liquid medium when the reducing agent is released in the liquid medium.

Although multi-layered (including core and coating layering) tablets or pills are preferred, the delayed release form of the present compositions can be present in any other suitable item or items, such as masses of powders, granules and the like. Delayed release technology is well known in the art as exemplified by the text *Controlled Drug Delivery*, 2nd Ed., Joseph R. Robinson & Vincent H. L. Lee, Eds., Marcel Dekker, Inc., New York, 1987.

Items which release their ingredients in a sequential, time delayed manner are well known and can be produced using conventional technology. Therefore, a detailed description of such items and such production technology is not presented here. However, such items are preferably designed to allow the disinfectant component a period of time, more preferably a period of time sufficient to disinfect the lens in the liquid medium, before releasing the enzyme and disinfecting destroying component in the liquid medium. In other words, such components are preferably designed so that sufficient time elapses between initial contact with the liquid medium and release of the enzyme and disinfectant destroying component to allow the disinfectant to perform its function. Such sufficient time is preferably within about 6 hours, for example, in the range of about 1 minute to about 6 hours, more preferably within about 2 hours, for example, in the range of about 2 minutes to about 2 hours.

In one useful embodiment, a direct compression is made of the core tablet formulation using conventional tableting equipment. A solution containing the delayed release component is applied, e.g., sprayed, onto the core tablet using conventional coating equipment, such as film coating pans or fluid beds. Coating pan equipment is available from Driam of West Germany, Thomas Engineering, Vector Corporation, and Key Industries in the U.S. Fluid bed equipment is available from Glatt Air Techniques, Vector Corporation, and Aeromatic, as well as other companies. Using appropriate coating parameters, which are dependent on, for example, the specific composition of the delayed release component-containing solution, the equipment used and core tablet size, an appropriate amount of delayed release component is applied to the core tablet that allows the desired delay release time.

Any suitable delayed release component or combination of delayed release components may be employed, provided that such component or components function as described herein and have no substantial detrimental effect on the enzyme and disinfectant destroying component, on the lens being treated and on the human wearing the treated lens. The delayed release component is preferably at least partially, more preferably completely, water soluble. The delayed release component preferably comprises a major amount of at least one polymeric material. Examples of useful delayed release components include, but are not limited to, soluble cellulose ethers such as methylcellulose, methylhydroxypropylcellulose, methylhydroxyethylcellulose, hydroxypropylcellulose, hydroxyethylcellulose and sodium carboxymethylcelluloses; cellulose esters such as cellulose acetate phthalate and hydroxypropylmethylcellulose phthalate; polymers derived from at least one of acrylic acid, acrylic acid esters, methacrylic acid and methacrylic acid esters such as methacrylic acid-methyl methacrylate copolymer (for example that sold by Rohm Pharma under the trademark Eudragit L 100) and methacrylic acid-ethyl acrylate copolymers (for example that sold by Robin Pharma under the trademark Eudragit L 30D); polymers derived from methyl vinyl ether and maleic acid anhydride; polyvinylpyrrolidone; polyvinyl alcohols and the like and mixtures thereof.

The present composition may further comprise, e.g., as an outer layer or shell on a delayed release item, at least one activator component, such as an acidity component and/or an organic acid anhydride component or a transition metal component when the disinfectant is to be chlorine dioxide. The activator component is present in an amount effective to activate or promote the formation of the disinfectant component from a disinfectant component precursor, e.g., stabilized chlorine dioxide, in the liquid medium in which the composition is used. The composition is structured to release the activator component in the liquid medium prior to the release of the disinfectant destroying component in the liquid medium.

In one embodiment of the present invention, chlorine dioxide per se is the lens disinfectant. Preferably, the disinfecting is performed by chlorine dioxide in a liquid medium. Thus, chlorine dioxide itself, for example chlorine dioxide gas, may be dissolved in the liquid medium and used to disinfect the lens. However, it is often impractical or even impossible to dissolve sufficient gaseous chlorine dioxide in a liquid medium, e.g., saline, to be an effective contact lens disinfectant. In addition, a substantial amount of the dissolved chlorine dioxide is often very rapidly lost from the liquid medium.

In order to avoid these concerns, the liquid medium may, and preferably does, initially include at least one "precursor" of chlorine dioxide. Such precursors act in the liquid medium in response to one or more factors other than the presence of the lens to be disinfected to produce chlorine dioxide in a lens disinfecting amount. Chlorine dioxide per se and not, for example, a chlorine dioxide precursor, acts as the primary, preferably as the sole, disinfecting agent to disinfect the lens. As used herein, a disinfecting amount of chlorine dioxide means such amount as will reduce the microbial burden or load by one log order in 3 hours or less, preferably in 1 hour or less, and more preferably in 10 minutes or less.

In the event the liquid medium contains chlorine dioxide precursor, this medium is preferably substantially free of any quaternary ammonium salts, and positively charged, nitrogen-containing cationic polymers, such as those disclosed as having antimicrobial or germicidal properties in Stockel et al. U.S. Pat. Nos. 4,499,077 and 4,654,208. Among the positively charged, nitrogen-containing cationic polymers which have antimicrobial or germicidal properties are quaternary ammonium polymers, such as copolymers of at least one mono-or di-functional tertiary amine and a dihalo organic compound. Also included in such positively charged, nitrogen-containing cationic polymers are polymeric amino and/or imino compounds, such as polydiguanides.

In general, the chlorine dioxide precursors useful in the present invention are those which form or produce chlorine dioxide in a liquid medium, preferably a liquid aqueous medium, in response to at least one factor other than the presence of the lens to be disinfected. For example, such chlorine dioxide precursors may form or produce chlorine dioxide in the presence of certain transition metal-containing components or in the presence of certain organic acid anhydride components or in a reduced pH environment.

One method for generating chlorine dioxide in an aqueous medium comprises buffering the medium to between pH 6–10, that is to a pH of between about 6 to about 10, and exposing a stable chlorine dioxide precursor to at least one transition metal component, for example, for at least one minute.

Any transition metal component capable of effecting the release of chlorine dioxide from the precursor in an aqueous medium at a pH between 6–10, or possibly higher, may be employed. The primary criteria for such transition metal component is that it have the ability to effect formation of a disinfecting amount of chlorine dioxide from the described chlorine dioxide precursors. Such metal components should also have no substantial detrimental effect on the lens to be disinfected.

It is preferred that the metal component be present as a solid. In certain embodiments, solid metals can be easily and conveniently introduced into or removed from the chlorine dioxide precursor-containing liquid medium, as desired. Also a solid metal component can be readily separated from the solution for repeated use in disinfecting lenses. The metal component may be immobilized, or maintained substantially stationary, relative to the solution. The metal component may be positioned to contact the chlorine dioxide precursor-containing liquid medium as the liquid medium is introduced into the container in which the contact lens is to be disinfected.

The particular metals of interest herein are the transition metals and mixtures thereof, in particular from Group III metals, Group IV metals, Group V metals, Group VI metals, Group VII metals, Group VIII metals and mixtures thereof.

Because of their high degree of effectiveness, platinum group metals and mixtures thereof, and especially platinum or palladium, are particularly useful. The platinum group metals include platinum, palladium, Iridium, ruthenium, rhodium and osmium.

The metal component or components may be present in the metallic form and/or in a combined form as part of an organic or inorganic compound or complex.

The amount of metal component needed to practice this invention is to be viewed in terms of what quantity or surface area is useful to generate a particular concentration of chlorine dioxide in a given time and in light of the amount of precursor present in solution. It has been observed that the metal component is not used up in the process of generating chlorine dioxide. Thus, it may be assumed the metal acts as a catalyst to effect formation of the chlorine dioxide. But the chemistry has not been investigated other than to observe that the metal component apparently is not consumed in the process of creating chlorine dioxide.

Assuming the process is catalytic in nature, the amount of metal component surface area exposed to the solution should be taken into consideration. Specific surface area data can be readily determined by simply exposing a chlorite salt of one concentration to various metal components deposited on different surface areas, then observing the rate of chlorine dioxide formation. From there, actual working parameters can be generated. Transition metals useful herein can also be dispersed in the aqueous medium.

It is most convenient to place the metal components on some support device. Such supports are particularly useful if the metal component includes one or more platinum group metals, which are quite expensive. The support may be chosen so as to provide surface area on which the promotion component can be placed.

Any suitable support material may be employed, and preferably is substantially inert at the conditions employed in the present invention. Examples of support materials include polymeric materials (plastics), metals, aluminas, silicas, clays, ceramics and the like. The supported promotion component may have any suitable shape or configuration, such as sheets, rods, extrudates, tablets, pills, irregular shaped particulars, spheres, disks and the like. Any of a number of conventional techniques can be employed to deposit the metal-containing component on the support material. These techniques include impregnation, co-precipitation, ion-exchange, dipping, spraying, vacuum depositions and the like.

During the disinfecting contacting, it is preferred that the aqueous medium have a pH in the range of about 6 to about 10, but more preferably about 7.5. Such more preferred pH ranges are substantially consistent with the normal physiological pH for humans. Thus, after disinfecting, the disinfected lens may be placed directly in the eye.

This embodiment may be practiced at a pH lower than 6. At that pH, and lower, chlorine dioxide is generated from chlorites and many stabilized chlorine dioxides by virtue of the lower pH. In essence, the precursor is not stable for very long at these lower pHs at standard temperature and pressure. So formulating a composition for use at some remote time such as is often encountered with consumer products where the shelf life of the product must be many months means this aspect of the invention has certain formulation limitations. But is has been found that a transition metal component will increase the amount of chlorine dioxide generated at lower pHs, as well as the rate at which it is generated. If such highly acidic conditions are employed, a neutralization step may be useful to neutralize any acidic residue which may remain in or on the lens. Neutralization can be easily accomplished by rinsing or soaking the disinfected lens in a neutral or slightly basic saline solution.

In one embodiment, a lens to be disinfected is contacted with a composition including a liquid medium, at least one chlorine dioxide precursor and at least one organic acid anhydride component in an amount sufficient to effect formation of chlorine dioxide from the precursor. This contacting results in the lens being disinfected. When, as is preferred, an aqueous liquid medium is preferred, the pH of this medium may be alkaline, neutral or acidic.

Any suitable organic acid anhydride component may be employed. The primary criteria for such component is that it have the ability to effect formation or generation of chlorine dioxide, preferably contact lens disinfecting amounts of chlorine dioxide, from chlorine dioxide precursor in a liquid medium. Such organic acid anhydride components should also have no substantial detrimental effect on the lens to be disinfected.

Examples of useful organic acid anhydride components include succinic anhydride, glutaric anhydride, maleic anhydride and the like and mixtures thereof. The organic acid anhydride or anhydrides are preferably present during the disinfecting contacting in an amount in the range of about 0.01 mole or less to about 1 mole or more per mole of potential chlorine dioxide present as chlorine dioxide precursor in the liquid medium.

In the event the disinfecting contacting using organic acid anhydride or anhydrides is conducted in an acidic environment, after the disinfecting contacting the acidity of the liquid medium can be reduced in an acidity adjusting step, e.g., as described elsewhere herein.

In one embodiment, a lens to be disinfected is contacted with a composition including a liquid medium and at least one chlorine dioxide precursor, which contacting takes place in the presence of at least one acidic component in an amount sufficient to effect formation of chlorine dioxide from the precursor. This contacting results in the lens being disinfected. Thus, in mildly acidic conditions, in particular at a pH of less than about 6 and especially in the range of about 3 to about 5, the production of chlorine dioxide is effected.

Any suitable acidic component may be employed. The primary criteria for such component is that it have the ability to increase the acidity of the liquid medium containing at least one chlorine dioxide precursor sufficiently to effect formation of chlorine dioxide from such chlorine dioxide precursor, and preferably sufficiently to effect formation of lens disinfecting amounts of chlorine dioxide from the presently useful chlorine dioxide precursors. Such acidic components should also have no substantial detrimental effect on the lens to be disinfected.

Examples of the presently useful acidic components include mineral acids, salts of such mineral acids, carboxyiic acids, salts of such carboxylic acids and mixtures thereof. The mineral acids include, for example, nitric acid, sulfuric acid, hydrogen halides, phosphoric acid and the like. The carboxylic acids include both mono- and poly-, e.g., di-, tri-and the like, carboxylic acids, and preferably include 1 to about 10 carbon atoms per molecule. One or more non-hydrocarbonaceous groups, e.g., hydroxy groups, halide groups and the like, may be appended to the carboxylic acid. If an acid salt is employed, it is preferred that the salt be an alkali or alkaline earth metal salt, more preferably an alkali metal salt. A particularly useful group of acidic components is selected from alkali metal hydrogen phosphates, citric acid, lactic acid, tartaric acid and mixtures thereof.

During the disinfecting contacting, it is preferred that the liquid aqueous medium have a pH of about 6 or less, in particular in the range of about 3 to about 5.

After the disinfecting contacting, the disinfected lens is contacted with a liquid medium having reduced acidity relative to the liquid medium in the disinfecting contacting. For example, the acidity of the liquid medium used in the disinfecting contacting can be reduced in an acidity adjusting step, as described herein. In any event, after the acidity is reduced, the disinfected lens is preferably present in a liquid aqueous medium which preferably has a pH in the range of about 6.5 to about 8, and more preferably about 7.5. Such pH ranges are substantially consistent with the normal physiological pH for humans.

The present acidity adjusting step preferably provides for reducing the acidity of the liquid medium containing the disinfected lens. Thus, if the liquid medium is aqueous-based, the adjusting step preferably provides for increasing the pH of the disinfected lens-containing liquid medium. In one embodiment, an acidity adjusting component useful to reduce the acidity of the liquid medium is introduced into the liquid medium after the lens has been disinfected. However, this acidity adjusting component may be introduced into the liquid medium at substantially the same time as is the acidic component introduced into the liquid medium. The acidity adjusting component can be included in a delayed release form, e.g., tablet, pill or the like, designed to release the acidity adjusting component into the liquid medium after the pill or tablet is exposed to the liquid medium. For example, the acidity adjusting component can be included in a composition with the acidic component with the composition structured to release the acidity adjusting component into a liquid medium after the acidic component is released into the liquid medium.

The acidity adjusting component is preferably selected from the group consisting of basic components, buffer components and mixtures thereof. The acidity adjusting component may be a mixture of at least one basic component and at least one buffer component. The acidity adjusting component should have no substantial detrimental effect on the lens being treated. Examples of useful acidity adjusting components include borates, dibasic phosphates, carbonates, bicarbonates, mixtures thereof and the like. The acidity adjusting components preferably are compounds including alkali metals or alkaline earth metals, in particular alkali metals, especially sodium.

The amount of the acidity adjusting component or components employed is sufficient to achieve the desired acidity reduction in the liquid medium containing the lens, in particular the disinfected lens.

Among the preferred chlorine dioxide precursors useful in the present invention is stabilized chlorine dioxide. The term "stabilized chlorine dioxide" as used herein means one or more chlorine dioxide-containing complexes and/or one or more chlorite-containing components and/or one or more other entities capable of forming chlorine dioxide in a liquid medium in response to at least one factor other than the presence of the lens to be disinfected.

Examples of such chlorite-containing components include metal chlorites, and in particular alkali metal and alkaline earth metal chlorites. A specific example of a chlorite-containing component which is useful as a chlorine dioxide precursor is technical grade sodium chlorite. A/nong the preferred chlorine dioxide-containing complexes are complexes of chlorine dioxide with carbonate, chlorine dioxide with bicarbonate and mixtures thereof. The exact chemical composition of many of the chlorine dioxide precursors, e.g., stabilized chlorine dioxide, and in particular the chlorine dioxide complexes, is not completely understood. The manufacture or production of certain chlorine dioxide precursors is described in McNicholas U.S. Pat. No. 3,278,447, which is hereby incorporated in its entirety by reference herein. Specific examples of useful chlorine dioxide precursor sources include products such as that sold under the trademark Dura Klor by Rio Linda Chemical Company, Inc., and that sold under the trademark Anthium Dioxide by International Dioxide, Inc. An especially useful chlorine dioxide precursor source is a product sold under the trademark Purogene by BioCide International, Inc. The chlorine dioxide precursor may be included in a liquid medium at a predetermined concentration, e.g., a concentration chosen to provide a disinfecting amount of chlorine dioxide in response to at least one factor other than the presence of the lens to be disinfected. Preferably, the liquid medium has sufficient chlorine dioxide precursor so as to have a potential of producing chlorine dioxide in the range of about 0.002% to about 3% by weight, based on the total weight of the liquid medium including the chlorine dioxide precursor or precursors.

In one embodiment, the chlorine dioxide precursor includes a functionality selected from carbonate, borate, sulfate, phosphate, and mixtures thereof.

The liquid medium used is selected to have no substantial detrimental effect on the lens being treated and to allow, and preferably to even facilitate, the present lens treatment or treatments. The liquid medium is preferably aqueous-based. A particularly useful liquid aqueous medium is that derived from saline, e.g., a conventional saline solution.

The disinfecting and cleaning contactings preferably occur at a temperature to maintain the liquid medium substantially liquid. For example, when the liquid medium is aqueous-based, it is preferred that the contacting temperature be in the range of about 0° C. to about 100° C., and more preferably in the range of about 10° C. to about 60° C. Contacting at or about ambient temperature is very convenient and useful. The contactings preferably occur at or about atmospheric pressure. The disinfecting contacting preferably occurs for a time to substantially completely disinfect the lens being treated. Such contacting times can be in the range of about 0.1 hours to about 12 hours or more. The cleaning contacting preferably occurs for a time to substantially clean the lens of at least one type of debris, e.g., in the range of about 0.2 hours to about 12 hours or more.

In order to insure that the pH of the liquid aqueous medium is maintained within the desired range during the disinfecting and cleaning procedures, the liquid aqueous medium may include at least one buffer component. Although any suitable buffer component may be employed, if a chlorine dioxide precursor is employed it is preferred to select such component so as not to substantially detrimentally affect the desired formation of chlorine dioxide. It is preferred that the buffer component be inorganic.

Among the preferred buffer components are those which include phosphate functionalities, borate functionalities, carbonate functionalities and mixtures thereof. Particularly increased rates of chlorine dioxide formation are achieved, for example using a transition metal component to promote the generation of chlorine dioxide, when the buffer component includes phosphate functionalities, borate functionalities and mixtures thereof. Alkali metal and alkaline earth metal buffer components are advantageously used in the present invention.

The following non-limiting examples illustrate certain aspects of the present invention.

EXAMPLE 1

This example illustrates the effect of stabilized chlorine dioxide concentration on the production of chlorine dioxide.

A series of solutions was prepared using different concentrations of a stabilized chlorine dioxide product, sold by Bio-cide International, Inc. under the trademark Purogene. The stabilized chlorine dioxide product included 2.0% by weight of potential (ultimate yield) chlorine dioxide and 0.085% by weight of sodium carbonate.

Each of these solutions was prepared as follows:
(1) 0.1% (W/V) of boric acid was dissolved in deionized water to provide buffering;
(2) a calculated amount of sodium chloride was added so that the final solution was isotonic;
(3) the pH of the solution was adjusted to 7.5;
(4) the desired amount of the stabilized chlorine dioxide product was added; and
(5) the final volume of the solution was adjusted using deionized water.

Each of these solutions was tested as follows. A 10 ml. sample of the solution was placed in a plastic container at ambient temperature and pressure. A plastic disc, containing platinum as platinum oxide, was placed in the container in the solution. The actual concentration of chlorine dioxide in the solution was monitored at various times after the disc was placed in the container. Results of these tests were as follows:

TABLE 1

| Time (min) | Stabilized $ClO_2$ Product Concentrations, ppm. by wt. | | | | | | |
|---|---|---|---|---|---|---|---|
| | 0.0 | 50 | 100 | 250 | 500 | 750 | 1000 |
| | $ClO_2$ Concentration, ppm. by wt. | | | | | | |
| 0 | 0.0 | 0.00 | 0.00 | 0.00 | 0.00 | 0.00 | 0.00 |
| 30 | 0.0 | 0.74 | 0.99 | 1.80 | 3.76 | 6.40 | 6.31 |
| 60 | 0.0 | 0.94 | 1.61 | 5.11 | 6.11 | 8.19 | 10.79 |
| 90 | 0.0 | 1.09 | 1.66 | 3.72 | 10.93 | 8.46 | 12.28 |
| 120 | 0.0 | 0.90 | 1.81 | 4.06 | 12.08 | 11.80 | 12.78 |
| 240 | 0.0 | 1.13 | 1.26 | 4.95 | 8.10 | 11.18 | 19.19 |
| 480 | 0.0 | 1.00 | 1.28 | 4.08 | 5.17 | 10.23 | 13.78 |

These results indicate that the concentration of chlorine dioxide reaches a maximum and then begins to decrease with time. Further, the initial pH of each solution was about 7.5 and remained substantially unchanged throughout the test.

It has been reported that essentially no chlorine dioxide was detected in a borate buffered, 0.85% sodium chloride aqueous solution containing the above-noted stabilized chlorine dioxide product at a pH of 7.5. Thus, these results do demonstrate that platinum does effect formation of chlorine dioxide.

EXAMPLE 2

A solution containing deionized water, 0.85% (w/v) of sodium chloride, 0.10% (w/v) of boric acid, and 50 ppm w/v of the stabilized chlorine dioxide product identified in Example 1 was prepared. Each of the concentrations of stabilized chlorine dioxide product set forth in Examples 2 and 3 is stated in terms of potential chlorine dioxide. One portion of this solution was buffered to a pH of 7.9, while the other portion was buffered to a pH of 6.8. Varying amounts of tartaric acid was added to different samples of each of these portions. The samples were then tested, following the standard procedure, to determine the D-value with respect to various microorganisms. The D-value is defined as the length of time required to reduce the microbial burden or load by one log unit.

Results of these tests were as follows:

TABLE 2

| pH = 6.8 | | | | | |
|---|---|---|---|---|---|
| Tartaric Acid, ppm. | 30 | 40 | 50 | 60 | 70 |
| Free Chlorine Dioxide, ppm. | 10.74 | 17.08 | 37.94 | 25.38 | 32.47 |

TABLE 2-continued

| Microorganism | Extrapolated D-value at 23° C., min. | | | | |
|---|---|---|---|---|---|
| S. marcescens | <.84 | <.84 | <.84 | <.84 | <.84 |
| S. aureus | <.87 | <.87 | <.87 | <.87 | <.87 |
| P. aeruginosa | <.85 | <.85 | <.85 | <.85 | <.85 |
| A. fumigatus | <.83 | <.83 | <.83 | <.83 | <.83 |
| pH = 7.9 | | | | | |
| Tartaric Acid, ppm. | 30 | 40 | 50 | 60 | 70 |
| Free Chloride Dioxide, ppm. | 0.03 | 0.11 | 0.05 | 0.15 | 0.23 |
| Microorganism | Extrapolated D-value at 23° C., min. | | | | |
| S. marcescens | 5.13 | <.85 | 2.56 | <.85 | 2.56 |
| S. aureus | 10.17 | 2.54 | 2.54 | 12.24 | 2.54 |
| P. aeruginosa | 19.48 | <.87 | 2.6 | <.87 | <.87 |
| A. fumigatus | 109 | 109 | 150 | 162.2 | 70.6 |

These results of Examples 1 and 2 indicate that chlorine dioxide per se can be present in a sufficient amount in a liquid medium to be effective to disinfect contact lenses. Thus, these results demonstrate that sufficient chlorine dioxide can be provided in a liquid medium to reduce the microbial burden or load by one log order in a period of time generally deemed acceptable for disinfecting contact lenses.

EXAMPLE 3

A lens disinfecting system was provided which included a solution, an activator tablet and a neutralizer tablet.

The solution was purified water with the following components: 0.85% (w/v) sodium chloride; 0.10% (w/v) boric acid; and 0.005% (w/v) the stabilized chlorine dioxide product identified in Example 1. The pH of this solution is about 7.7 to 7.9.

The activator tablet had the following composition: 27.0 mg. tartaric acid; 10.0 mg. anhydrous sodium carbonate; 40.6 mg. sugar-based binder/filler; and 2.4 mg. polyethylene glycol (molecular weight of about 3350) (a conventional tableting lubricant).

The neutralizer tablet had the following composition: 3.0 mg. tartaric acid; 21.0 mg. sodium carbonate; 23.3 mg. sugar-based binder/filler; 1.5 mg. polyethylene glycol (molecular weight of about 3350); and 1.2 mg. N-acetylcysteine.

The activator tablet was placed in 10 ml. of the solution and the resulting material was monitored for pH and chlorine dioxide concentration. Chlorine dioxide appeared in 28±3 seconds. The pH of the material was noted at 3.6±0.1. After 5 minutes, the chlorine dioxide concentration was 43.62±0.38 ppm. After 30 minutes, the chlorine dioxide concentration was 41.12±0.92 ppm.

The neutralizer tablet was then placed in the material. The neutralizer tablet dissolved in the material. Upon shaking the material, the characteristic color of chlorine dioxide which was present disappeared immediately. The pH of the final solution was 6.61±0.03 and drifted up to about 7 after 30 minutes. The chlorine dioxide concentration of the final solution is 0.16±0.04 ppm.

The amount of chlorine dioxide produced by combining the activator tablet with the solution is effective to kill most microorganisms in about 10 minutes or less, e.g., about 1 to 2 minutes. Disinfection of soft contact lens can be accomplished in about 1 to 2 minutes. However, at this point, the solution has a disagreeable odor and color, a low pH and may contain sufficient chlorine dioxide to cause eye irritation.

The neutralizer tablet is added to the solution to raise the pH to a comfortable level and consume chlorine dioxide. A disinfected contact lens could be taken from the neutralized system and placed directly in the eye without irritation or discomfort. Alternately, the disinfected contact lens could be removed from the chlorine dioxide-containing solution and contacted, e.g., washed, with a buffered saline solution prior to being placed into the eye.

EXAMPLE 4

A lens disinfecting system is provided which includes the solution as identified in Example 3 and a core-type tablet. This core-type tablet is like a tablet within a tablet. The outer shell is the activator and the inner core is the neutralizer. The activator shell has the following composition: 27 mg. tartaric acid; 10 mg. anhydrous sodium carbonate; 60 mg. a conventional sugar—or sucrose—based bulking agent; and 3 mg. polyethylene glycol (molecular weight of about 3350). The neutralizer core has the following composition: 5 mg. tartaric acid, 35 mg anhydrous sodium carbonate; 3 mg N-acetylcysteine; 15.2 mg. sugar-based binder/filler and 1.8 mg. polyethylene glycol (molecular weight of about 3350).

When this core-type tablet is introduced into 10 ml. of the solution, the activator shell rapidly dissolves and the pH is lowered to 3 to 4. Chlorine dioxide is generated. After the entire activator shell has dissolved, e.g., in about 2 to 5 minutes, the neutralizer core dissolves so that in another additional 2 to 3 minutes substantially all of the chlorine dioxide is removed from the solution and the pH is raised to a level of about 6.5 to 7.9.

The present disinfecting system is effective to disinfect a soft contact lens.

EXAMPLE 5

A lens disinfecting system is provided which is the same as that in Example 4 except for the composition of the neutralizer core.

In the present system, the neutralizer core has the following composition: 8.2 mg. tartaric acid; 57.8 mg. anhydrous sodium carbonate; 4.5 mg. N-acetylcysteine; 2.4 mg. polyethylene glycol (molecular weight of about 3350); 6.39 mg. sugar-based binder/filler; and 0.71 mg. Subtilisin A (an enzyme conventionally used to clean contact lenses).

This system functions in much the same manner as the system of Example 4 except that the Subtilisin A is released with the other components of the neutralizer core. Thus, after the pH of the solution is raised to about 6.5 to 7.9, enzymatic cleaning of the lens in the solution begins. The enzyme can be inactivated by chlorine dioxide. However, the chlorine dioxide is removed from the solution sufficiently rapidly so that the enzyme remains effective to clean the lens.

EXAMPLE 6

A core tablet is produced by direct compression using conventional tableting equipment and has the following composition:

| | mg |
|---|---|
| Subtilisin A | 0.4 |
| Sugar-based binder/buffer | 21.6 |
| N-acetylcysteine | 1.0 |
| Sodium carbonate(anhydrous) | 25.0 |
| Tartaric acid | 10.0 |
| Polyethylene glycol | 2.0 |
| (molecular weight of | |

|  | mg |
|---|---|
| about 3350) | |
| Total | 60.0 |

A delayed release coating solution is prepared and has the following composition:

|  | w/w % |
|---|---|
| Polymer[1] | 6.25 |
| triethylcitrate | 0.47 |
| Isopropyl alcohol | 93.28 |
| Total | 100.00 |

[1]A methyl acrylate-methacrylic acid copolymer sold by Rohm Pharma under the trademark Eudragit L 100.

The coating solution is sprayed onto the core tablet using conventional coating equipment, such as a film coating pan. An appropriate amount of coating material is applied to the core tablet to produce a coated tablet in which the release of the core tablet into a chlorine dioxide-containing liquid aqueous solution is effectively delayed for a sufficient time, on the order of about 30 minutes, after the coated tablet is first introduced into the solution to allow the chlorine dioxide to perform appropriate disinfection, for example, of a contact lens. In order to achieve an approximately 30 minute delay for a core tablet 5.2 mm in diameter and 2.2 nun thick, the coated tablet contains about 5 to about 10 mg (per tablet) of coating derived from the above-noted coating solution.

EXAMPLE 7

A contact lens is disinfected and cleaned as follows. A contact lens and the coated tablet produced in Example 6 are placed into 10 ml. of the solution identified in Example 3 in a container. Before being placed in the container the solution is passed across a platinum-containing screen to generate an effective disinfecting amount of chlorine dioxide in the solution. In about 10 minutes or less after the contact lens and tablet are introduced into the solution, the contact lens is disinfected. About 30 minutes after the contact lens and tablet are introduced into the solution, the coating on the tablet is completely dissolved, and the contents of the core are released in the solution to chemically reduce the residual chlorine dioxide in the solution and to enzymatically clean the contact lens. About two hours after the contact lens and coated tablet are introduced into the solution, the disinfected/cleaned lens is removed from the solution, is rinsed free of residual enzyme and loosened deposits with a conventional saline solution and is placed in the lens wearer's eye for safe and comfortable wear.

EXAMPLE 8

Example 6 is repeated except that the core tablet has the following composition:

|  | mg |
|---|---|
| Subtilisin A | 0.5 |
| Sugar-based binder/filler | 30.0 |
| N-acetylcysteine | 15.0 |
| Sodium carbonate (anhydrous) | 20.0 |
| Polyethylene glycol | 2.0 |
| (molecular weight of about 3350) | |
| | 67.5 |

A coated tablet having delayed release characteristics similar to those set forth in Example 6 is produced.

EXAMPLE 9

Example 7 is repeated using the coated tablet produced in Example 8 in place of the coated tablet produced in Example 6.

About two hours after the contact lens and coated tablet are introduced into the solution, the disinfected/cleaned lens is removed from the solution, is rinsed free of residual enzyme and loosened deposits with a conventional saline solution and is placed in the lens wearer's eye for safe and comfortable wear.

EXAMPLE 10

Example 6 is repeated except that the delayed release coating solution has the following composition:

|  | w/w % |
|---|---|
| Hydroxypropylmethyl cellulose[1] | 3.37 |
| Polyethylene glycol (molecular weight of about 300) | 0.67 |
| Isopropyl alcohol | 18.48 |
| Water, purified | 77.48 |
| Total | 100.00 |

[1]Sold by Dow Chemical Company under the trademark Methocel.

A coated tablet having delayed release characteristics similar to those set forth in Example 6 is produced.

EXAMPLE 11

Example 7 is repeated using the coated tablet produced in Example 10 in place of the coated tablet produced in Example 6.

About two hours after the contact lens and coated tablet are introduced into the solution, the disinfected/cleaned lens is removed from the solution, is rinsed free of residual enzyme and loosened deposits with a conventional saline solution and is placed in the lens wearer's eye for safe and comfortable wear.

EXAMPLE 12

Example 8 is repeated except that the delayed release coating solution identified in Example 10 is used. A coated tablet having delayed release characteristics similar to those set forth in Example 6 is produced.

EXAMPLE 13

Example 7 is repeated using the coated tablet produced in Example 12 in place of the coated tablet produced in Example 6.

About two hours after the contact lens and coated tablet are introduced into the solution, the disinfected/cleaned lens is removed from the solution, is rinsed free of residual enzyme and loosened deposits with a conventional saline solution and is placed in the lens wearer's eye for safe and comfortable wear.

EXAMPLE 14

Example 6 is repeated except that the delayed release coating solution has the following composition:

|  | w/w % |
| --- | --- |
| Hydroxypropylmethyl cellulose[1] | 3.5 |
| Polyethylene glycol (molecular weight of about 300) | 0.7 |
| Water, purified | 95.8 |
| Total | 100.0 |

[1] Sold by Dow Chemical Company under the trademark Methocel.

A coated tablet having delayed release characteristics similar to those set forth in Example 6 is produced.

EXAMPLE 15

Example 7 is repeated using the coated tablet produced in Example 14 in place of the coated tablet produced in Example 6.

About two hours after the contact lens and coated tablet are introduced into the solution, the disinfected/cleaned lens is removed from the solution, is rinsed free of residual enzyme and loosened deposits with a conventional saline solution and is placed in the lens wearer's eye for safe and comfortable wear.

EXAMPLE 16

Example 8 is repeated except that the delayed release coating solution identified in Example 14 is used. A coated tablet having delayed release characteristics similar to those set forth in Example 6 is produced.

EXAMPLE 17

Example 7 is repeated using the coated tablet produced in Example 16 in place of the coated tablet produced in Example 6.

About two hours after the contact lens and coated tablet are introduced into the solution, the disinfected/cleaned lens is removed from the solution, is rinsed free of residual enzyme and loosened deposits with a conventional saline solution and is placed in the lens wearer's eye for safe and comfortable wear.

EXAMPLE 18

Example 6 is repeated except that the delayed release coating solution has the following composition

|  | w/w % |
| --- | --- |
| Polymer[1] | 50 |
| triethylcitrate | 2 |
| Water, purified | 48 |

[1] An ethyl acrylate-methacrylic acid copolymer in aqueous dispersion sold by Rohm Pharma under the trademark Eudragit L 30D.

A coated tablet having delayed release characteristics similar to those set forth in Example 6 is produced.

EXAMPLE 19

Example 7 is repeated using the coated tablet produced in Example 18 in place of the coated tablet produced in Example 6.

About two hours after the contact lens and coated tablet are introduced into the solution, the disinfected/cleaned lens is removed from the solution, is rinsed free of residual enzyme and loosened deposits with a conventional saline solution and is placed in the lens wearer's eye for safe and comfortable wear.

EXAMPLE 20

Example 8 is repeated except that the delayed release coating solution identified in Example 18 is used. A coated tablet having delayed release characteristics similar to those set forth in Example 6 is produced.

EXAMPLE 21

Example 7 is repeated using the coated tablet produced in Example 20 in place of the coated tablet produced in Example 6.

About two hours after the contact lens and coated tablet are introduced into the solution, the disinfected/cleaned lens is removed from the solution, is rinsed free of residual enzyme and loosened deposits with a conventional saline solution and is placed in the lens wearer's eye for safe and comfortable wear.

EXAMPLE 22

Example 6 is repeated except that the delayed release coating solution is sprayed onto the core tablet so as to form a sub-coated tablet having a thin coating of the coating material. Example 6 is again repeated except that this sub-coated tablet is used in place of the core tablet, and the coating solution of Example 14 is used in place of the coating solution of Example 6.

A coated tablet having delayed release characteristics similar to those set forth in Example 6 is produced.

EXAMPLE 23

Example 7 is repeated using the coated tablet produced in Example 22 in place of the coated tablet produced in Example 6.

About two hours after the contact lens and coated tablet are introduced into the solution, the disinfected/cleaned lens is removed from the solution, is rinsed free of residual enzyme and loosened deposits with a conventional saline solution and is placed in the lens wearer's eye for safe and comfortable wear.

EXAMPLE 24

Example 22 is repeated except that the coating solution of Example 18 is used in place of the coating solution of Example 6.

A coated tablet having delayed release characteristics similar to those set forth in Example 6 is produced.

EXAMPLE 25

Example 7 is repeated using the coated tablet produced in Example 24 in place of the coated tablet produced in Example 6.

About two hours after the contact lens and coated tablet are introduced into the solution, the disinfected/cleaned lens is removed from the solution, is rinsed free of residual enzyme and loosened deposits with a conventional saline solution and is placed in the lens wearer's eye for safe and comfortable wear.

While this invention has been described with respect to various specific examples and embodiments, it is to be understood that the invention is not limited thereto and that it can be variously practiced within the scope of the following claims.

What is claimed is:

1. A composition comprising an effective debris removing amount of an enzyme component effective in removing debris from a contact lens, and a chlorine dioxide destroying component effective in destroying chlorine dioxide, said enzyme component being included in said composition relative to said chlorine dioxide destroying component so that said enzyme component is released in a liquid medium containing chlorine dioxide substantially at the same time or after said chlorine dioxide destroying component is released in said liquid medium to destroy chlorine dioxide contained in said liquid medium, thereby allowing said enzyme component to remove debris from a contact lens in said liquid medium; said chlorine dioxide destroying component being present in an amount effective to destroy all the chlorine dioxide contained in said liquid medium.

2. The composition of claim 1 which comprises a delayed release component in an amount effective to delay the release of said enzyme component and said chlorine dioxide destroying component in said liquid medium for a period of time after said composition is initially contacted with said liquid medium, said period of time being sufficient so that a contact lens which is initially contacted with said liquid medium at the same time said composition is initially contacted with said liquid medium is disinfected prior to the time said chlorine dioxide destroying component is released in said liquid medium.

3. The composition of claim 2 wherein said delayed release component is present in a single coating substantially surrounding one or both of said enzyme component and said chlorine dioxide destroying component.

4. The composition of claim 2 wherein said delayed release component is selected from the group consisting of cellulose ethers, cellulose esters, polymers derived from at least one of acrylic acid, acrylic acid esters, methacrylic acid and methacrylic acid esters, polymers derived from methyl vinyl ether and maleic acid anhydride, polyvinylpyrrolidone, polyvinyl alcohols and mixtures thereof.

5. The composition of claim 2 which further comprises an activator component in an amount effective to activate the formation of chlorine dioxide from a chlorine dioxide precursor in said liquid medium, said activator component being included in said composition relative to said chlorine dioxide reducing component so that said activator component is released in said liquid medium prior to the release of said chlorine dioxide destroying component in said liquid medium.

6. The composition of claim 1 wherein said enzyme component is released in said liquid medium at substantially the same time as said chlorine dioxide destroying component is so released.

7. The composition of claim 1 wherein said composition is in the form of a tablet or a pill.

8. The composition of claim 1 wherein said enzyme component is selected from the group consisting of proteolytic enzymes, carbohydrate-active enzymes and mixtures thereof.

9. The composition of claim 1 wherein said enzyme component is selected from the group consisting of proteases, amylases, lipases and mixtures thereof.

10. The composition of claim 1 wherein said chlorine dioxide destroying component is selected from the group consisting of reducing agents capable of chemically reducing chlorine dioxide in said liquid mediums and mixtures thereof.

11. A composition comprising an enzyme component effective in removing debris from a contact lens and a disinfectant destroying component effective in destroying said contact lens disinfectant, said contact lens disinfectant being incompatible with said enzyme component, said enzyme component being included in said composition relative to said disinfectant destroying component so that said enzyme component is released in a liquid medium containing said contact lens disinfectant at substantially the same time or after said disinfectant destroying component is released in said liquid medium to destroy said contact lens disinfectant contained in said liquid medium, thereby allowing said enzyme component to remove debris from a contact lens in said liquid medium, said disinfectant destroying component being present in an amount effective to destroy all said contact lens disinfectant contained in said liquid medium.

12. The composition of claim 11 which comprises a delayed release component in an amount effective so that neither said enzyme component nor said disinfectant destroying component is released in said liquid medium for a period of time after said composition is initially contacted with said liquid medium, said period of time being sufficient so that a contact lens which is initially contacted with said liquid medium at the same time said composition is initially contacted with said liquid medium is disinfected prior to the time said disinfectant destroying component is released in said liquid medium.

13. The composition of claim 12 wherein said delayed release component is effective so that said enzyme component is released in said liquid medium after said disinfectant destroying component is so released.

14. The composition of claim 12 wherein said delayed release component is present in a coating substantially surrounding one or both of said enzyme component and disinfectant destroying component.

15. The composition of claim 12 wherein said delayed release component is selected from the group consisting of cellulose ethers, cellulose esters, polymers derived from at least one of acrylic acid, acrylic acid esters, methacrylic acid and methacrylic acid esters, polymers derived from methyl vinyl ether and maleic acid anhydride, polyvinylpyrrolidone, polyvinyl alcohols and mixtures thereof.

16. The composition of claim 11 wherein said composition is in the form of a tablet or a pill.

17. The composition of claim 11 wherein said enzyme component is selected from the group consisting of proteolytic enzymes, carbohydrate-active enzymes, lipases and mixtures thereof, and said contact lens disinfectant is selected from the group consisting of chlorine dioxide, potassium peroxymonosulfate and quaternary ammonium disinfectants.

18. A method for removing debris from a contact lens comprising:
   contacting a contact lens with a liquid medium containing a disinfectant component in the presence of a composition comprising an enzyme component which is incompatible with said disinfectant component and is effective in removing debris from a contact lens and a disinfectant destroying component effective in destroying said disinfectant component after being released in said liquid medium, said disinfectant destroying component being present in an amount effective to destroy all said disinfectant component in said liquid medium; and
   releasing said enzyme component and said disinfectant destroying component from said composition in said liquid medium and removing debris from said contact lens in said liquid medium, said enzyme component being released in said liquid medium substantially at the same time or after said disinfectant destroying component is released in said liquid medium.

19. The method of claim 18 wherein said composition comprises a delayed release component in an amount effective to delay the release of said enzyme component and said disinfectant destroying component in said liquid medium for a period of time after said composition is initially contacted with said liquid medium, said period of time being sufficient so that a contact lens which is initially contacted with said liquid medium at the same time said composition is initially contacted with said liquid medium is disinfected prior to the time said disinfectant destroying component is released in said liquid medium.

20. The method of claim 18 wherein said enzyme component is released in said liquid medium after said disinfectant destroying component is so released.

21. The method of claim 18 wherein said enzyme component is selected from the group consisting of proteolytic enzymes, carbohydrate active enzymes, lipases and mixtures thereof.

22. The method of claim 18 wherein said disinfectant component comprises chlorine dioxide.

23. The method of claim 22 wherein said disinfectant destroying component comprises a reducing agent effective to chemically reduce chlorine dioxide and said enzyme component is released in said liquid medium at substantially the same time as said disinfectant destroying component is so released.

24. The method of claim 18 wherein said enzyme component is selected from the group consisting of proteolytic enzymes, carbohydrate-active enzymes, lipases and mixtures thereof, and said contact lens disinfectant is selected from the group consisting of chlorine dioxide, potassium peroxymonosulfate and quaternary ammonium disinfectants.

25. The method of claim 19 wherein said delayed release component is selected from the group consisting of cellulose ethers, cellulose esters, polymers derived from at least one of acrylic acid, acrylic acid esters, methacrylic acid and methacrylic acid esters, polymers derived from methyl vinyl ether and maleic acid anhydride, polyvinylpyrrolidone, polyvinyl alcohols and mixtures thereof.

* * * * *

UNITED STATES PATENT AND TRADEMARK OFFICE
CERTIFICATE OF CORRECTION

PATENT NO. : 5,338,480
DATED : August 16, 1994
INVENTOR(S) : Dziabo et al

It is certified that error appears in the above-indentified patent and that said Letters Patent is hereby corrected as shown below:

Column 1, line 51; delete "canbe" and insert in place thereof --can be--.

Column 3, line 4; delete "enzymeS" and insert in place thereof --enzymes--.

Column 3, line 6; delete line 6 and insert --enzymes. Specific examples of useful enzymes include--.

Column 3, line 9; delete "sulfhydryt" and insert in place thereof --sulfhydryl--.

Column 6, line 9; delete "Robin" and insert in place thereof --Rohm--.

Column 7, line 46; delete "lridium" and insert in place thereof --iridium--.

Column 9, line 36; delete "acid." and insert in place thereof --acid,--.

Column 10, line 49; delete "A/nong" and insert in place thereof --Among--.

Column 15, line 29; delete "nun" and insert in place thereof --mm--.

Column 19, line 39; delete "reducing" and insert in place thereof --destroying--.

Column 22, line 10; delete "contact lens" and after "disinfectant" insert --component--.

UNITED STATES PATENT AND TRADEMARK OFFICE
CERTIFICATE OF CORRECTION

PATENT NO. : 5,338,480
DATED : August 16, 1994
INVENTOR(S) : Dziabo et al

It is certified that error appears in the above-indentified patent and that said Letters Patent is hereby corrected as shown below:

Column 22, line 11; after "factant" and insert --component--.

Column 19, line 6; delete ";" and insert in place thereof --,--.

Signed and Sealed this

Twenty-second Day of October, 1996

Attest:

BRUCE LEHMAN

Attesting Officer

Commissioner of Patents and Trademarks